(12) United States Patent
Tsai

(10) Patent No.: US 6,312,737 B1
(45) Date of Patent: Nov. 6, 2001

(54) **METHOD OF INDUCING APOPTOSIS IN CANCER CELLS USING AN EXTRACT OF *MELOTHRIA INDICA* LOU**

(75) Inventor: David Tsai, Westlake Village, CA (US)

(73) Assignee: Ambryx Biotechnology, Inc.

( * ) Notice: Subject to any disclaimer, the term of this patent is extended or adjusted under 35 U.S.C. 154(b) by 0 days.

(21) Appl. No.: 09/568,625

(22) Filed: May 10, 2000

(51) Int. Cl.[7] .......................... A01N 65/00; A01N 61/00; A61K 35/78; A61K 39/385
(52) U.S. Cl. .............. 424/758; 424/725; 514/1; 514/908
(58) Field of Search .................. 424/195.1, 725, 424/758; 514/908, 1

(56) References Cited

FOREIGN PATENT DOCUMENTS

40915938A * 12/1997 (JP).
10114670A * 5/1998 (JP).

OTHER PUBLICATIONS

Krammer, P.H., et. al., Apoptosis in the APO–1 System Apoptosis: The Molecular Basis of Cell Death, 1991, pp. 87–99, Cold Spring Harbor Lab. Press.

Kerr, J.F.R. and Searle, J., A Suggested Explanation for the Paradoxically slow growth rate of basal–cell Carcinomas . . . , J. Path., vol. 107, p. 41–44, (1971).

Michaelson, J., Cell Selection in Development, Biol. Rev. (1987), vol. 62, p.115–139, Great Britain.

Wyllie, A.H., et al., Cell Death: The Significance of Apoptosis, International Review of cytology, vol. 68, p. 251–306, Academic Press, 1980.

Cope, F., et al., Apoptosis: The Molecular Basis of Cell Death, Cold Spring Harbor Laboratory Press, p. 61–86, 1991: "Carciogenesis and Apoptosis: Paradigms . . . ".

* cited by examiner

Primary Examiner—Christopher R. Tate
Assistant Examiner—Michele Flood
(74) Attorney, Agent, or Firm—Trojan Law Offices

(57) ABSTRACT

The invention includes a method of inducing apoptosis in cancer cells by administering an extract of *Melothria indica* Lou to the cancer cells. The invention also includes a method of using an extract of *Melothria indica* Lou to induce apoptosis in cancer cells by administering the extract to the cancer cells. The cancer cells can be leukemia cells and prostate cancer cells. Further included in the invention is a method for purifying the *Melothria indica* Lou into an extract used for inducing apoptosis in cancer cells.

4 Claims, 6 Drawing Sheets

Fig. 7: Results of partially purified extract on mice injected with leukemia cells

| Group | Number of Mice | Dose | Survivors: Number of Mice (Days) | Increased Life Span (ILS) |
|---|---|---|---|---|
| I | 10 | 0.002 ml extract | 2 (30) | 25% |
| II | 10 | 0.02 ml extract | 4 (35) | 45% |
| III | 10 | 0.2 ml extract | 9 (60) | 150% |
| IV | 10 | 0.5 ml saline | 0 (24) | baseline |

Fig. 8: Results of highly purified extract on mice injected with prostate cancer cells

| Group | Number of Mice | Dose for Five Days | Result |
|---|---|---|---|
| I | 10 | 0.2 ml saline | All mice exhibited tumors |
| II | 6 | 0.01 ml extract | No tumor exhibited |
| III | 6 | 0.1 ml extract | No tumor exhibited |
| IV | 6 | 0.2 ml extract | No tumor exhibited |

METHOD OF INDUCING APOPTOSIS IN CANCER CELLS USING AN EXTRACT OF *MELOTHRIA INDICA* LOU

BACKGROUND OF THE INVENTION

1. Field of the Invention

This invention relates generally to cancer treatment and more specifically, to cancer treatments which selectively induce apoptosis in cancer cells.

2. Description of Related Art

Cancer was generally treated with combinations of surgery, chemotherapy and radiation with varying degrees of success. One way cancer has been targeted for treatment is that cancer cells tend to be rapidly dividing cells. Thus, current chemotherapeutic approaches target rapidly dividing tumor cells. This approach is generally ineffective when the cancer is dormant or slow growing. These types of treatments also impact other, noncancerous cells that divide rapidly, causing harmful side effects.

These harmful side effects, however, are not present in treatments that induce apoptosis in the cancer cells. Apoptosis is also called "programmed cell death" or "cell suicide." (Krammer, et al., "Apoptosis in the APO-1 System", Apoptosis: The molecular Basis of Cell Death, pp. 87–99 Cold Spring Harbor Laboratory Press, 1991). In contrast to the cell death caused by cell injury, apoptosis is an active process of gene-directed, cellular self-destruction. Apoptosis serves a biologically meaningful function. (Kerr, J. F. R. and J. Searle, J. Pathol. 107:41, 1971).

One of the examples of the biologically meaningful functions of apoptosis is the morphogenesis of an embryo. (Michaelson, J., Biol. Rev. 62:115, 1987). Just like creating a sculpture, clay is added, and clay is removed; organ formation (morphogenesis) of an embryo relies on cell growth (addition of clay) as well as cell death (removal of clay). As a matter of fact, apoptosis plays a key role in the human body from the early stages of embryonic development through to the inevitable decline associated with old age. (Wyllie, A. H., Int. Rev. Cytol. 68:251, 1980).

The normal function of the immune, gastrointestinal and hematopoietic system relies on the normal function of apoptosis. When the normal function of apoptosis goes awry, the result can be any of the following diseases: cancer, viral infections, autoimmune disease/allergies, neurodegeneration or cardiovascular diseases.

The idea that cancer may be caused by insufficient apoptosis emerged only recently (Cope, F. O. and Wille, J. J., "Apoptosis": The Molecular Basis of Cell Death, Cold Spring Harbor Laboratory Press, p. 61, 1991). This idea opens a door for a new concept in cancer therapy—cancer cells may be killed by encouraging apoptosis. Apoptosis modulation, based on the processes present in normal development, is a potential mechanism for controlling the growth of tumor cells. Restoring apoptosis in tumor cells is an attractive approach because it programs the cancer cells to commit suicide.

Thus, the cancer cells can be killed without killing the host. The success of this treatment, however, is dependent upon the availability of drugs that can selectively induce apoptosis in tumor cells without affecting normal cells.

From the preceding descriptions, it is apparent that the compositions and methods currently being used have significant disadvantages. Thus, important aspects of the technology used in the field of invention remain amenable to useful refinement.

SUMMARY OF THE INVENTION

The present invention introduces such refinement. In its preferred embodiments, the present invention has several aspects or facets that can be used independently, although they are preferably employed together to optimize their benefits.

*Melothria indica* Lou (Melothria) is a perennial berbaceous vine that thrives on hillsides and in the woods and bushes. Melothria, which emerged recently, is a popular herb in Taiwan, China and India and is believed to be beneficial in the treatment of sore throats, acute conjunctivitis and inflammation.

We have discovered, however, that the Melothria extract selectively induces apoptosis in cancer cells.

Thus, the invention includes a method of inducing apoptosis in cancer cells by administering an extract of *Melothria indica* Lou to the cancer cells, with the greatest apoptotic effects known at this time occurring in leukemia cells and prostate cancer cells. The invention also includes a method of using an extract of *Melothria indica* Lou to induce apoptosis in cancer cells by administering the extract to the cancer cells.

The invention further includes a method for purifying *Melothria indica* Lou, which comprises the following steps:

Extracting the *Melothria indica* Lou with a solvent to form an extract, concentrating the extract, applying the extract to a SCD-100 reverse phase chromatography column equilibrated with phosphate buffer saline, developing the SCD-100 column using an isocratic elution of phosphate buffer saline for about forty (40) minutes with a flow rate of about 0.4 ml/min, collecting at least fraction eleven (11) from the column, applying fraction eleven to a RPP-100 reverse-phase chromatography column equilibrated with 0.1% trifluoroacetic acid in water, developing the column by a linear gradient using solvent A and solvent B, solvent A being 0.1% trifluoroacetic acid in water and solvent B being water/$CH_3CN$/0.1% trifluoroacetic acid in a ratio of 49.5:49.5:1, generating a gradient using 100% solvent A and 0% solvent B at time zero, then increasing solvent B from 0% to 100% after 20 ml elution volume, collecting at least fraction two from the column, applying fraction two to a AX-100 anion exchange chromatography column equilibrated with solvent C, solvent C being 10% phosphate buffer saline in water, eluting the column with a solvent gradient including solvent C and solvent D, solvent D being 100% phosphate buffer saline, the solvent gradient is created starting with 100% solvent C and 0% of solvent D at time zero, then increasing solvent D from 0% to 100% after 20 ml elution volume, collecting at least fraction 12 from the column, applying fraction twelve to a silica gel column equilibrated with a solvent E, solvent C being $CH_3CN$:ethanol:water at a ratio of 84.5:15:0.5, isocratically eluting the column with solvent C, collecting at least fractions eight and nine.

All of the foregoing operational principles and advantages of the present invention will be more fully appreciated upon consideration of the following detailed description, with reference to the appended drawings.

BRIEF DESCRIPTION OF THE DRAWINGS

FIG. 7 shows the results of the partially purified extract of *Melothria indica* Lou on mice injected with leukemia cells; and FIG. 8 shows the results of the highly purified extract on mice injected with prostate cancer cells.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

In its preferred embodiment, the invention includes an extract of *Melothria indica* Lou ("Melothriaff") that selectively induces apoptosis in cancer cells. When the extract of Melothria was administered to leukemia cells (HL-60, ATCC cell line CCL 240), the characteristics of apoptosis were observed, both morphologically and biochemically, in approximately ninety percent (90%) of the leukemia cells.

After the leukemia cells were incubated with the Melothria, DNA was extracted from the leukemia cells and run on an agarose DNA Gel, and the "DNA ladder" was observed. The DNA ladder is indicative of cellular apoptosis. To corroborate that the leukemia cells were undergoing apoptosis, they were incubated with the Melothria for one (1) hour and then stained with Hoescht dye for one (1) hour.

Under fluorescent light, the nuclei of the leukemia cells show the characteristics of apoptosis. The nuclei have condensed, and the nuclear condensation is accompanied by the fragmentation of the DNA. Both of these occurrences are the morphological characteristics of cells undergoing apoptosis.

The Melothria extract was also administered to normal cells (CCD 39 Lu, ATCC cell line CRL 1498). The Melothria did not induce apoptosis in the normal cells. None of the characteristics of apoptosis were detected in the normal cells after they had been incubated with the Melothria for sixteen (16) hours. Thus, the Melothria extract selectively induced apoptosis in the leukemia cells and not the normal cells.

When the Melothria was administered to prostate cancer cells (LNCaP, ATCC cell line CRL 1740), the characteristics of apoptosis were observed. Although, the rate at which the Melothria induced apoptosis was slower with the prostate cancer cells than the leukemia cells. When the prostate cells were incubated with Melothria, the earliest time at which apoptosis was observed was after approximately five (5) hours of incubation.

Figure 1:
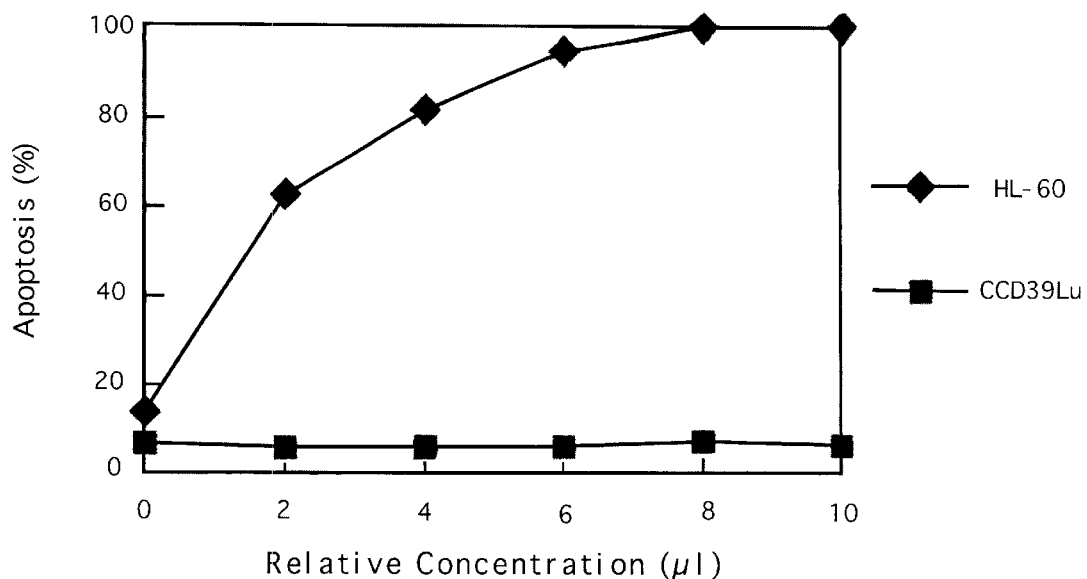
FIG. 1 shows that the increase in the concentration of the extract of *Melothria indica* Lou increases the apoptotic effect in leukemia cells.
Figure 2:
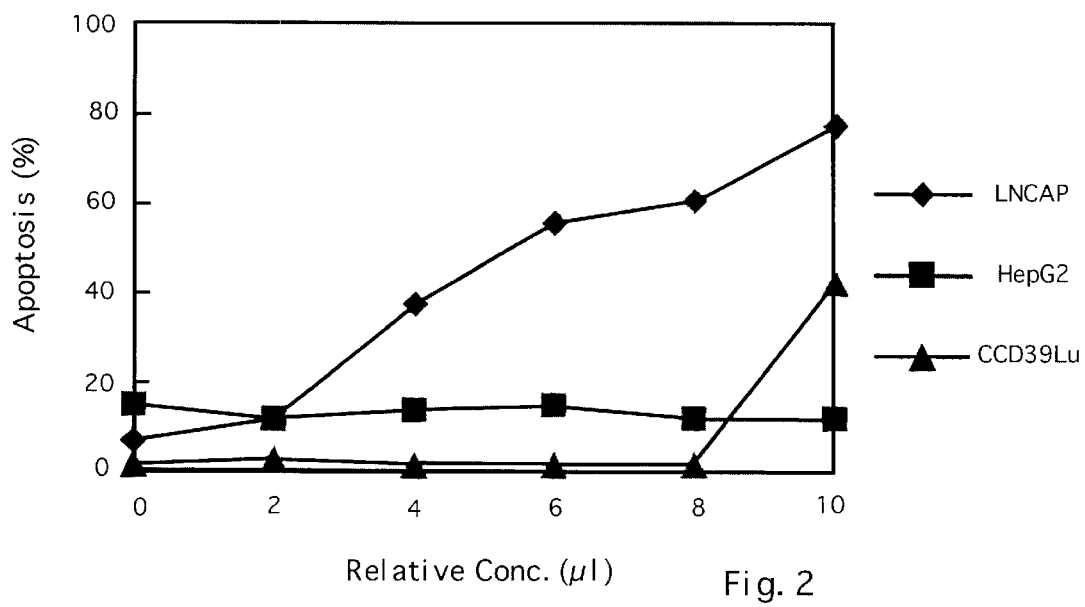
FIG. 2 shows that the increase in concentration of the extract of *Melothria indica* Lou increases the apoptotic effect in prostate cancer cells.

Melothria induces apoptosis in a dose dependent manner, as the dosage increases the percentage of cancer cells that undergo apoptosis correspondingly increases. As the concentration of the extract increases, the percentage of cancer cells undergoing apoptosis increases. (See FIGS. 1 and 2).

Purification

Purification of the Melothria extract was performed to find the active component in the extract. To partially purify the Melothria, fifty milliliters (50 ml) of hot water was added to ten grams (10 grams) of the fruit of *Melothria indica* Lou. The Melothria fruit and hot water steeped for about ten (10) minutes. The solution was concentrated into one milliliter (1 ml) using a SpeedVac. The concentrated solution was then passed through a Synchropak SCD-100 column. The column was equilibrated with phosphate buffer saline (PBS) and then developed by an isocratic elution of PBS for forty (40) minutes with a flow rate of 0.4 ml/min.

Figure 3:
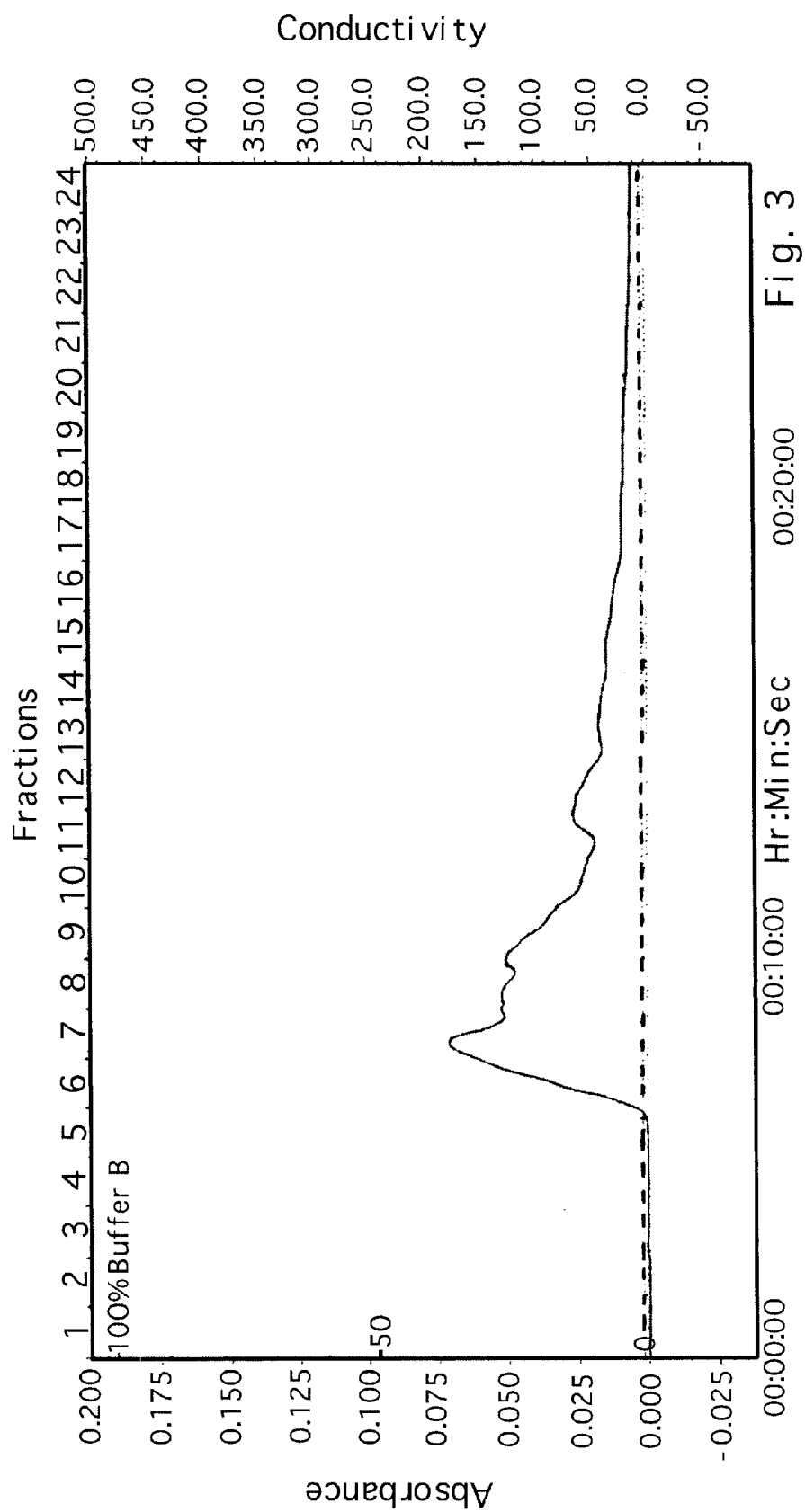
FIG. 3 shows the fractionation of the extract by SCD HPLC chromatography.

Each of the resulting fractions, one through twenty-four, was collected and then tested on the leukemia cells. Fraction 11 induced apoptosis in the leukemia cells. Fraction 11 was then further purified using a RPP-100 reverse-phase column (Micra Scientific, Inc. Northbrook, Ill.). (See FIG. 3).

Figure 4:
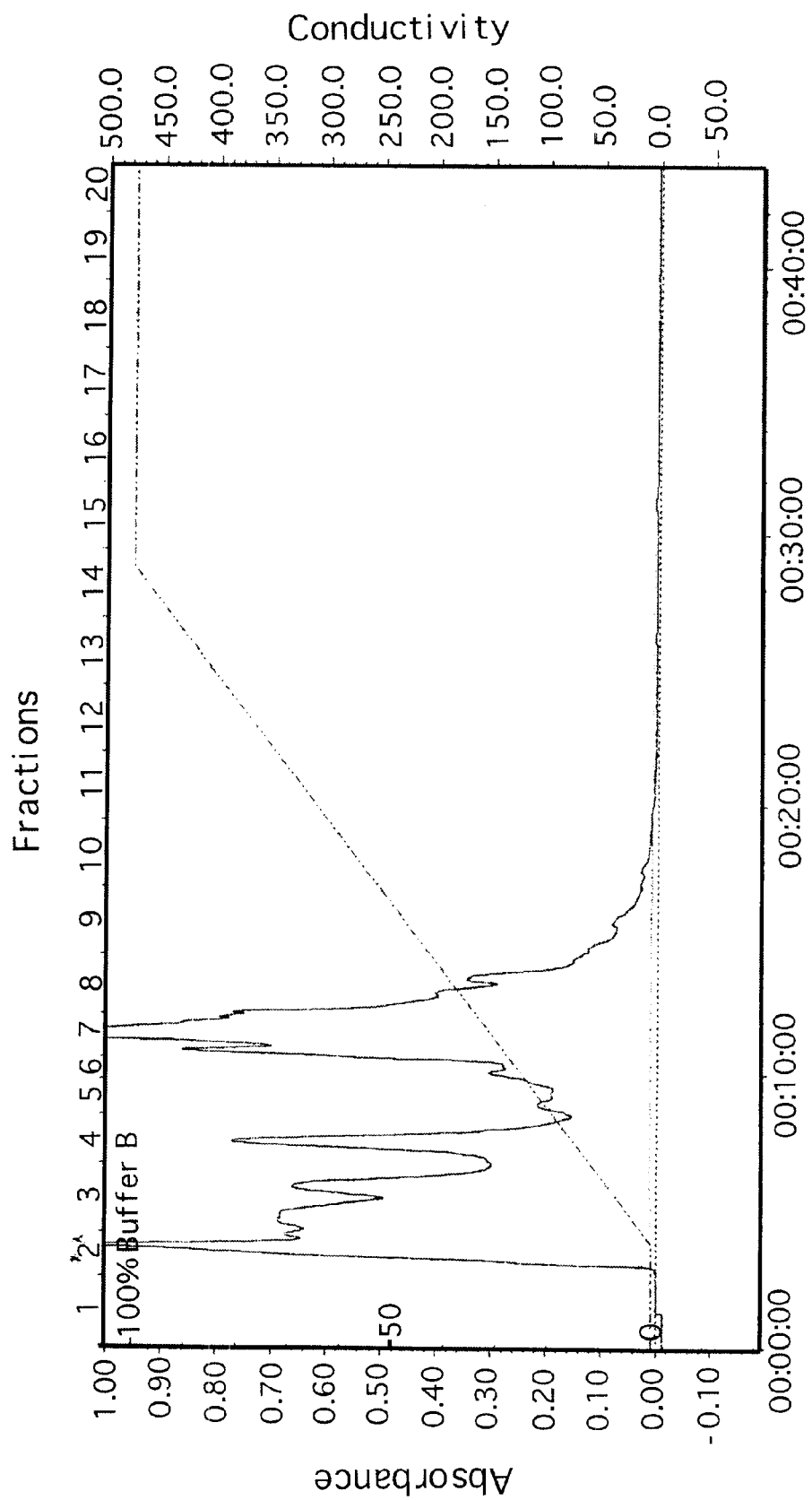
FIG. 4 shows the fractionation of the extract of *Melothria indica* Lou by RPP-100 reverse phase chromatography.

One milliliter (1 ml) of the concentrated active component present in fraction 11 was applied to the RPP-100 equilibrated with 0.1% Trifluoroacetic acid (TFA) in water. The column was developed using a linear gradient created by solvent A and solvent B. Solvent A is 0.1% TFA in water and solvent B is $H_2O:CH_3CN:0.1\%$ TFA having a ratio of 49.5:49.5:1. The gradient was generated by applying 100% solvent A and 0% solvent B at time zero (0), followed by increasing solvent B from 0% to 100% after 20 ml elution volume. Fraction 2 of the elution profile induces apoptosis in the leukemia cells. (See FIG. 4).

Figure 5:
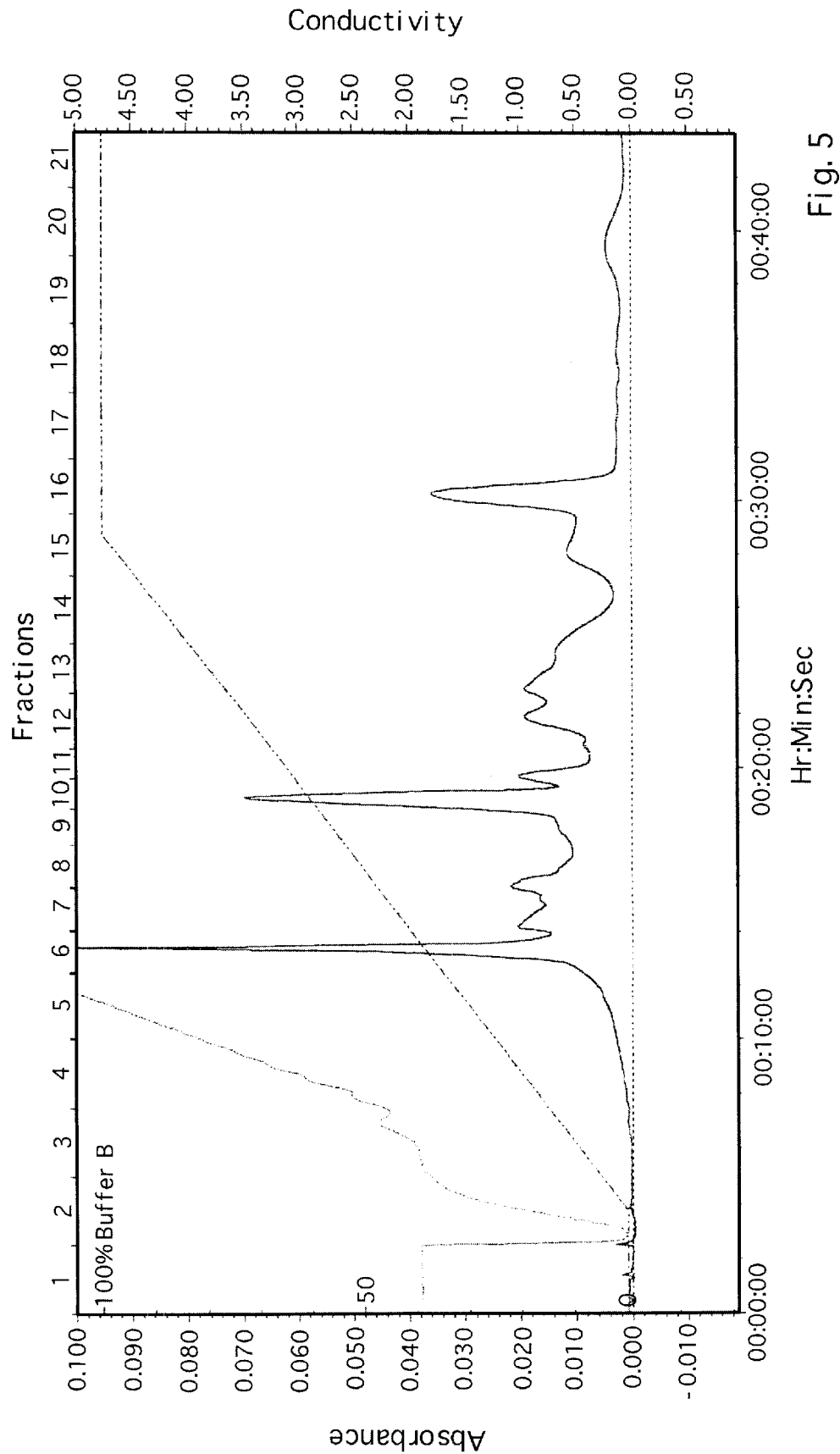
FIG. 5 shows the fractionation of the extract of *Melothria indica* Lou by anion exchange chromatography.

To further purify the extract, fraction 2 was applied to an AX-100 anion exchange chromatography column (Micra Scientific Inc., Northbrook, Ill.). The AX-100 was equilibrated with 1:10 $H_2O$ dilution of PBS, solvent C. The column was then eluted with a gradient created by 10% PBS in water, solvent C, and 100% PBS, solvent D. The gradient was created using 100% solvent C and 0% solvent D at time zero (0) followed by increasing solvent D from 0% to 100% after 20 ml elution volume. Fraction 12 of the elution profile induced apoptosis in prostate cancer cells (LNCaP) and the leukemia cells (HL-60). (See FIG. 5).

Figure 6:
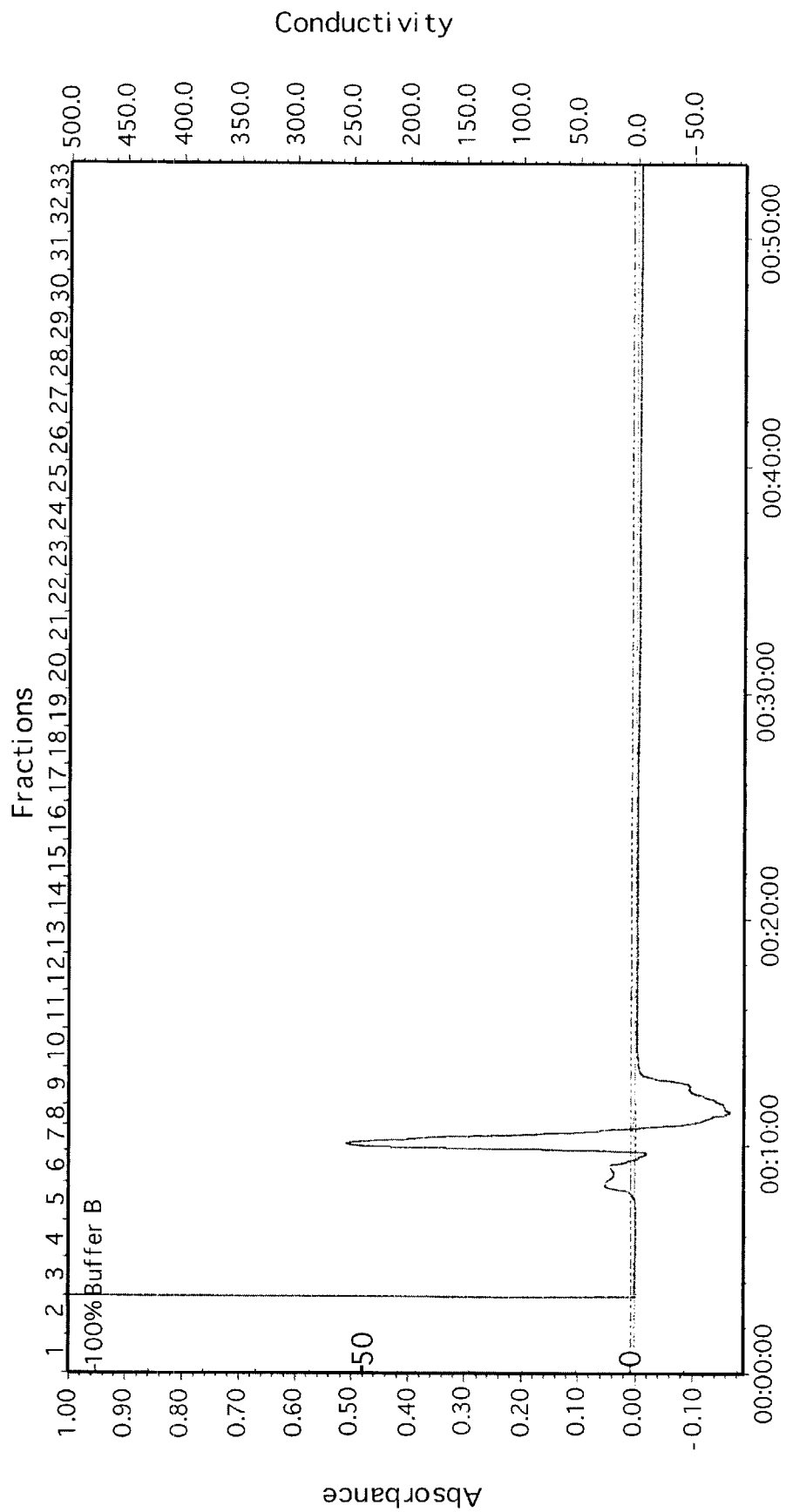
FIG. 6 shows the fractionation of the extract of *Melothria indica* Lou by silica gel absorption chromatography.

To purify the extract even further, fraction 12 was applied onto a silica gel column (Partisil 5, Whatman) which was equilibrated with $CH_3CN:Ethanol:H_2O$ having a ratio of 84.5:15:0.5, solvent E. The column was isocratically eluted with solvent E. Fraction 8 and fraction 9 of the elution profile induced apoptosis in prostate cancer cells and leukemia cells. Fractions 8 and 9 include the active component of the extract in a highly purified form. (See FIG. 6).

Testing and Results of Partially Purified Extract

A test was run using extract that had been partially purified by the SCD-100 column. The partially purified extract of *Melothria indica* Lou increased the life span of leukemia-bearing mice. Forty (40) DBA/2 female mice (17–20 grams; Simonsen Laboratories, Inc., Gilroy, Calif.) were inoculated with the tumor cell line P388D1 (ATCC Cell Line CCL 46). The tumor cells were harvested and diluted with saline. Then, the tumor cells were checked for viability using the trypan-blue staining technique. Each mouse was injected intraperitoneally with one million tumor cells. The mice were then segregated into four groups of ten mice. The mice were housed in shoe box cages and kept on a standard diet with water ad libitum.

Fraction 11 of the partially purified Melothria extract described above, was intraperitoneally injected into three of the groups. Each of the three groups was injected with different dosages of the extract. The fourth group was injected with saline.

$$ILS = 100 \times \frac{\text{median life span of treated mice} - \text{median life span of control mice}}{\text{life span of control mice}}$$

Referring to FIG. 7, Group I received a 0.002 ml dose of fraction 11, which increased the life span of the mice by twenty-five percent (25%). Group II received a 0.02 ml dose of fraction 11, which increased the life span of the mice by forty-five percent (45%). Group III received a 0.2 ml dose of fraction 11, which increased the life span of the mice by one hundred fifty percent (150%). Group IV received 0.5 ml of saline solution and provides the life span from which the increased life span is determined. The induction of apoptosis is dose dependent, as the dose of the fraction 11 material is increased, the life span of the mice also increases. (See FIG. 7).

Testing and Results of Highly Purified Extract

Highly purified extract was used in an in vivo study using mice with prostate cancer. Referring to FIG. 8, on day one, NIH nude adult male mice (TACH:NA (S)-NuFDF Homozygous males 3–4 weeks old) were inoculated with human prostate adenocarcinoma tumor cells (PC-3, ATCC Cell Line CRL 1435). On day two (2), Group I, the control group, received 0.2 ml of saline injected intraperitoneally for five (5) days. Group II received 0.01 ml of the extract, Group III received 0.1 ml and Group IV received 0.2 ml of the extract for five days.

The mice weighed an average of 22 g at the start of the experiment, and 30 g at the end of the experiment six (6) weeks later. After six weeks elapsed, the mice were examined, and the tumors were weighed. No tumors developed on the mice given the extract, groups II, III, and IV. Each mouse in the control group, however, developed tumors. Thus, the purified extract completely inhibited the formation of tumors in the mice. (See FIG. 8).

I claim:

1. A method of inducing apoptosis in leukemia cells by administering an extract of fruit of *Melothria indica* Lou to a subject in an effective amount to induce apoptosis of said leukemia.

2. The method of claim 1 wherein the subject is suffering from human leukemia.

3. A method of using an extract of fruit of *Melothria indica* Lou to induce apoptosis in prostate cancer cells by administering the extract to a subject in an effective amount to induce apoptosis of said prostate cancer.

4. The method of claim 3 wherein the subject has human prostate cancer.

* * * * *